US012605307B2

(12) United States Patent
Utterodt et al.

(10) Patent No.: US 12,605,307 B2
(45) Date of Patent: Apr. 21, 2026

(54) DENTAL COMPOSITE MATERIAL

(71) Applicant: KULZER GMBH, Hanau (DE)

(72) Inventors: Andreas Utterodt, Neu-Anspach (DE); Christoph Meier, Bruchkoebel (DE); Nelli Schoenhof, Braunfels (DE); Jutta Schneider, Runkel (DE); Kurt Reischl, Merenberg (DE); Raif Kocoglu, Graevenwiesbach (DE); Michael Eck, Schmitten (DE)

(73) Assignee: Kulzer GmbH, Hanau (DE)

( * ) Notice: Subject to any disclaimer, the term of this patent is extended or adjusted under 35 U.S.C. 154(b) by 829 days.

(21) Appl. No.: 17/773,261

(22) PCT Filed: Oct. 29, 2020

(86) PCT No.: PCT/EP2020/080364
§ 371 (c)(1),
(2) Date: Apr. 29, 2022

(87) PCT Pub. No.: WO2021/083992
PCT Pub. Date: May 6, 2021

(65) Prior Publication Data
US 2024/0164995 A1 May 23, 2024

(30) Foreign Application Priority Data
Oct. 31, 2019 (DE) ..................... 10 2019 129 550.5

(51) Int. Cl.
*A61K 6/893* (2020.01)
*A61K 6/17* (2020.01)
(Continued)

(52) U.S. Cl.
CPC ................ *A61K 6/893* (2020.01); *A61K 6/17* (2020.01); *A61K 6/76* (2020.01); *A61K 6/77* (2020.01);
(Continued)

(58) Field of Classification Search
CPC .... A61K 6/893; A61K 6/887; A61K 6/76–79; C08L 33/08; C08L 33/10
See application file for complete search history.

(56) References Cited

U.S. PATENT DOCUMENTS 4,744,827 A 5/1988 Winkel et al.
6,030,606 A * 2/2000 Holmes .................. A61K 6/893 424/49
(Continued)

FOREIGN PATENT DOCUMENTS

EP 0209700 A2 1/1987
EP 2436365 A2 4/2012

OTHER PUBLICATIONS

Yin Mei et al. "Preparation and characterization of Bis-GMA free dental resin system with synthesized dimethacrylate monomer TDDMMA derived from tricyclo[5.2.1.0(2,6)]-decanedimethanol", Journal of the Mechanical Behavior of Biomedical Materials, Elsevier, Amsterdam, NL, vol. 57, Dec. 17, 2015 (Dec. 17, 2015), pp. 157-163.
(Continued)

*Primary Examiner* — Kregg T Brooks
*Assistant Examiner* — David R. Foss
(74) *Attorney, Agent, or Firm* — Norris McLaughlin, P.A.

(57) ABSTRACT

The invention relates to a polymerisable dental composite material comprising
(i) 40 to 90% by weight of an inorganic filler component comprising at least one dental glass, as well as optionally at least one an amorphous metal oxide,
(ii) 10 to 60% by weight of at least one urethane (alkyl) acrylate of the idealised formula I,
(iii) 0.01 to 15% by weight of at least one di-, tri-, tetra- or multi-functional monomer not being a urethane (alkyl) acrylate,
(Continued)

a b (iv) 0.01 to 10% by weight of at least one initiator, of an initiator system, as well as optionally of at least one stabiliser, and optionally of at least one pigment, the total composition of the composite material amounting to 100% by weight, as well as to a polymerised composite material for producing direct dental restorations or indirect dental restorations.

8 Claims, 1 Drawing Sheet

(51) Int. Cl.

| | |
|---|---|
| ***A61K 6/76*** | (2020.01) |
| ***A61K 6/77*** | (2020.01) |
| ***A61K 6/78*** | (2020.01) |
| ***A61K 6/79*** | (2020.01) |
| ***A61K 6/887*** | (2020.01) |
| ***C08L 33/08*** | (2006.01) |
| ***C08L 33/10*** | (2006.01) |

(52) U.S. Cl.
CPC .................. *A61K 6/78* (2020.01); *A61K 6/79* (2020.01); *A61K 6/887* (2020.01); *C08L 33/08* (2013.01); *C08L 33/10* (2013.01)

(56) References Cited

U.S. PATENT DOCUMENTS

| | | | | |
|---|---|---|---|---|
| 9,023,916 | B2 | 5/2015 | Bloemker et al. | |
| 2012/0082958 | A1 * | 4/2012 | Blomker ................ | A61K 6/836<br>522/182 |

OTHER PUBLICATIONS

Kathrin Eitel et al. "A Hitchhiker's Guide to Particle Sizing Techniques" Langmuir, US, vol. 36, No. 35, Aug. 10, 2020 (Aug. 10, 22020), pp. 10307-10320.

* cited by examiner

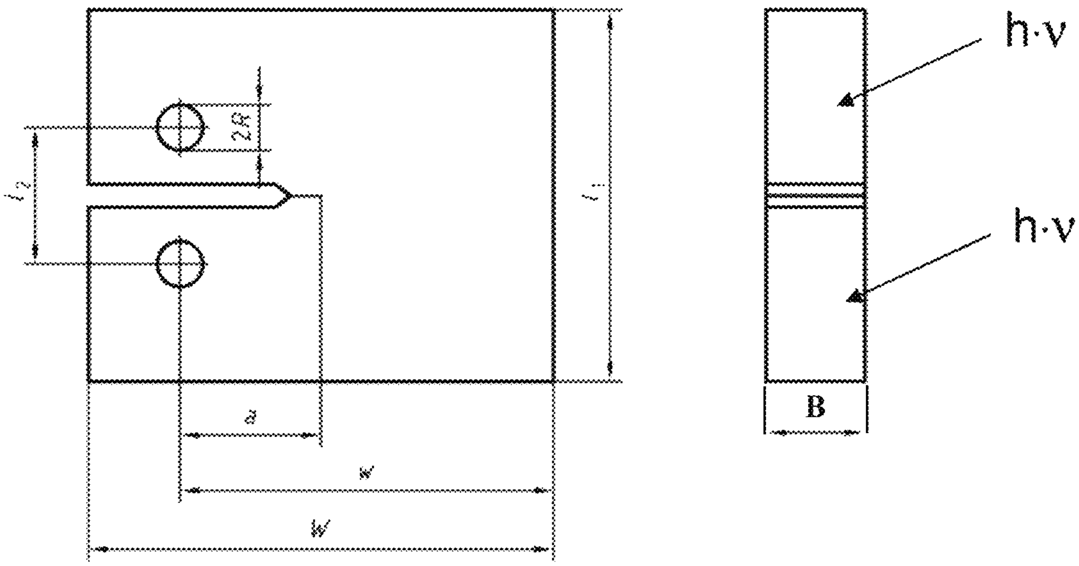
a b

DENTAL COMPOSITE MATERIAL

This application is a 371 of International Patent Application No. PCT/EP2020/080364, filed Oct. 29, 2020, which claims priority of German Patent Application No. 10 2019 129 550.5, filed Oct. 31, 2019, the disclosures of which patent applications are hereby incorporated herein by reference.

The invention relates to a polymerisable dental composite material, comprising (i) 40 to 90% by weight of at least one inorganic filler component comprising at least one dental glass of an average particle size $d_{50}$ of 0.5 to 10 μm, in particular of 0.7 to 7.5 μm, as well as optionally at least one amorphous metal oxide, (ii) 10 to 60% by weight of at least one urethane (alkyl) acrylate of formula I, in particular of a mixture of at least two different urethane (alkyl) acrylates, in particular urethane (meth-)acrylates, (iii) 0.01 to 15% by weight of at least one di-, tri-, tetra- or multi-functional monomer not being a urethane (alkyl) acrylate, in particular not being a urethane (meth-)acrylate, and (iv) 0.01 to 10% by weight of at least one initiator, of an initiator system, as well as optionally stabilisers, and optionally pigments, the total composition of the composite material amounting to 100% by weight, and to a polymerised composite material having a high fracture toughness und preferably a high flexural strength.

Many dental composites universally usable for a direct adhesive restoration as well as for the extraoral fabrication of indirect dentures are known. From the material class of dental composites, only inorganic-organic hybrid materials with larger amounts of inorganic filling materials such as e.g. dental glass and/or mineral nano agglomerates are suitable. Micro filler composites with pre-polymer fillers introduced in the 1980s are not suitable for use in the posterior region (classes I and II) due to the limited material tolerance (flexural strength).

Commercially available dental composites are usually based on cross-linking monomers having a structural unit of bisphenol (e.g. bis-GMA, bis-EMA) and further monomers with viscosity-reducing effect (e.g. TEGDMA, UDMA, etc.). Dental composites not having BPA structural units may be obtained using radically cross-linking TCD urethane monomers, additionally featuring significantly improved fracture toughnesses >1.0 MPa·$m^{0.5}$ (ISO 13586:2000). This surprisingly high fracture toughness (1.5 . . . 2.4 MPa·$m^{0.5}$) suggests advantages in long-term use since fracture of dental composites under chewing pressure is still a common reason for failure of this restorative class of materials.

A high filler content is advantageous in order to achieve very good mechanical properties of the cured composite and to reduce the polymerisation shrinkage that occurs during curing at the same time. These properties are also decisive for the long-term success of the denture material.

The excellent material properties of dental composites of esters with polyalicyclic structural elements for direct adhesive restoration, especially the low shrinkage force and high flexural strength, are well known.

It was the object of the invention to provide a dental composite material being suitable for producing dental filling materials as well as also for producing large blocks of material, in particular of geometric moulded bodies such as milling blocks. Additionally, the composite material shall have good values for fracture toughness representing a measure for the force to be applied for crack propagation in a material. In addition, it was the object to provide a dental composite material having a homogeneous, monochrome colouring before and after polymerisation. In this context, not only when producing dental filling materials but also a homogeneous, monochrome colouring should be feasible with larger blocks of material. Furthermore, polychrome, i.e. multi-coloured blocks of material with a defined colouring should be producible. Moreover, a dental composite material should be provided that shows sufficient flow properties in non-polymerised state and yet may be transferred in a polymerised state with excellent mechanical properties by means of UV radiation or visible light. A dental composite material having a low shrinkage in the polymerised state, even when producing larger blocks of material, should be provided also. Furthermore, the composite material should not develop cracks or pores during curing, even with large-volume blocks of material.

Starting from state-of-the-art composites, a new composite material with a new urethane derivative having a tricycle was developed. The invention relates to composite material as disclosed herein, to a polymerised composite material as disclosed herein, as well as to the use thereof, wherein preferred embodiments are disclosed in detail in the description.

The particle size distribution can be rather wide for a high filling material packaging density and excellent mechanical properties or rather tight for specific applications, depending on the desired filler content. The average value of the particle size distribution can be in the range of 0.5 μm to 10 μm, preferably in a range of 0.7 μm to 7.5 μm. In this context, the particle size distribution can be set based on a content of 5 to 75% by weight of a dental glass having a particle size distribution of $d_{50}$ of a dental glass fraction in the range of 0.7 μm to 2.0 μm, in particular 1.2 to 2.0 μm (micrometers), based on the total composition, preferably with $d_{50}$ of 1.8 μm with plus/minus 0.25 μm, particularly preferably $d_{99}$ less than or equal to 20 μm or $d_{99}$ less than or equal to 10 μm. In alternatives, further dental glass fractions having different smaller and/or larger particle size distributions can be added to adjust the packing density optimally. The adjusted packing density enables optimal setting of the mechanical properties and of a reduced shrinkage.

Composites having reduced shrinkage and good flexural strength of TCD esters are known. Surprisingly, very good value for fracture toughness (measured according to ISO 13586:2000) could be shown for radiation-cured composites comprising polymerisation products of urethanes of the idealised formula I, in particular of the idealised formula Ia, preferably after radiation curing. Likewise, surprisingly good values for flexural strength (measured according to ISO 13586:2000) could be obtained for thermally cured composites comprising polymerisation products of urethanes of the idealised formula I.

Surprisingly, it has been found that composites based on a urethane monomer having an alicyclic structural element, such as tetrahydrodicyclopentadiene, are extremely well suited for producing indirect dentures, since surprisingly high flexural strengths (according to DIN ISO 404902019) may be achieved even by photochemically initiated polymerization. The high level of material strength compared to the already described photopolymerization of light-curing dental composites was surprising and not to be expected with these significantly increased values.

A subject matter of the invention is a polymerisable dental composite material, in particular a photoinitiatedly polymerisable composite material, comprising (i) 40 to 90% by weight, in particular from 70 to 90% by weight, of at least one inorganic filler component comprising at least one dental glass, in particular of an average particle size $d_{50}$ of 0.5 μm to 10 μm, preferably 0.7 to 7.5 μm, in particular of 0.7 μm to 5.5 μm, preferably of 0.8 μm to 5.5 μm, as well as optionally at least one amorphous metal oxide, in particular with 2 to less than 10% by weight, preferably from 2 to 7.5% by weight, amorphous metal oxide, based on the total composition, (ii) 10 to 60% by weight, in particular 10 to 30% by weight, preferably 12 to 20% by weight, of at least one urethane acrylate comprising at least one urethane acrylate having a bivalent alicyclic group of the idealised formula I, preferably comprising a mixture of at least two different urethane acrylates, in particular of a mixture of at least one di-functional urethane acrylate or di-functional urethane alkyl acrylate having a bivalent alicyclic group comprising a urethane of the idealised formular I alkylene group preferably comprising di-functional urethane alkyl acrylates having a bivalent alkylene group with alkyl 1 to 10 C-atoms and alkylene 3 to 20 C atoms.

A particularly preferred dental composite material comprises (i) 70 to 85% by weight of an inorganic filler component comprising at least one dental glass, as well as optionally at least one amorphous metal oxide, (ii) 10 to 30% by weight of a mixture of at least two different urethane acrylates, the mixture comprising at least one di-functional urethane acrylate and/or urethane alkyl acrylate having a bivalent alicyclic group comprising a urethane of the idealised formula I and/or mixtures of said urethanes of formula I, as well as optionally mixtures of the isomers of the afore-mentioned compounds with mit $R^1$ and $R^2$ each independently selected from H and alkyl with 1 to 8 C atoms,

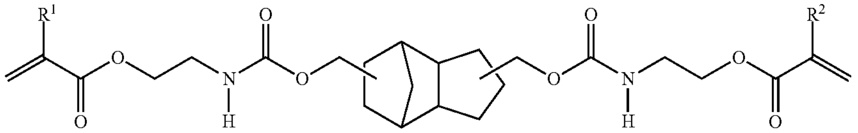

I and/or mixtures of the urethanes of formula I, as well as optionally mixtures of isomers of the urethanes of formula I (see also formular Ia), in particular mixtures of the 3,8-/3,9-/4,8-/3,10-/4,10-isomers and/or of the cis- and trans-isomers of the afore-mentioned compounds, with $R^1$ and $R^2$ each independently selected from H and alkyl with 1 to 8 C atoms, preferred is a mixture of at least three different urethane acrylates and/or urethane alkyl acrylates, in particular comprising di- to deca-functional urethane acrylates, (iii) 0.01 to 15% by weight, in particular from 0.01 to 5% by weight, at least one di-, tri-, tetra- or multi-functional monomer not being a urethane acrylate or urethane (alkyl) acrylate, in particular not being a urethane (meth)acrylate, (iv) 0.01 to 10% by weight of at least one initiator, of an initiator system, as well as optionally of at least one stabiliser, and optionally of at least one pigment, in particular the at least one pigment comprising fluorescence as well as colour pigment, the total composition of the composite material amounting to 100% by weight.

The urethanes of the idealised formula I are listed under cas no. 94 5656-78-0 (2-propenoic acid, 1,1'-[(octahydro-4,7-methano-1H-indene-5,?-diyl) bis(methylene oxycarbonyl amino-2,1-ethanediyl)] ester). Alternatively, the formula may be illustrated as follows.

(iii) 0.01 to 5% by weight of at least one di-, tri-, tetra- or multi-functional monomers not being a urethane acrylate and/or urethane alkyl acrylate, (iv) 0.01 to 10% by weight of at least one initiator, of an initiator system, as well as optionally of at least one stabiliser, and optionally of at least one pigment, the total composition of the composite material amounting to 100% by weight.

A further particularly preferred composite material comprises (i) 70 to 85% by weight of at least one inorganic filler component comprising at least one dental glass comprising barium aluminium borosilicate glass, barium aluminium borofluor silicate glass, and/or a feldspar, in particular silanised, preferably functionalised with methacryloyloxy propyl groups, in particular of an average particle size $d_{50}$ of 0.5 μm to 10 μm, preferably 0.7 to 7.5 μm, in particular of 0.7 μm to 5.5 μm, preferably of 0.8 μm to 5.5 μm, as well as optionally greater than 1 to 10% by weight, preferably 2 to 7.5% by weight, particularly preferably 3 to 7.5% by weight, a non-agglomerated amorphous metal oxide of a primary particle size of 2 to 150 nm, in particular of 2 to 100 nm, preferably of 2 to 45 nm, the amorphous metal oxide comprising silicon dioxide, precipitated silicon dioxide, pyrogenic silica, zirconium oxide, mixed oxides or mixtures thereof, in particular the metal oxides are silanised,

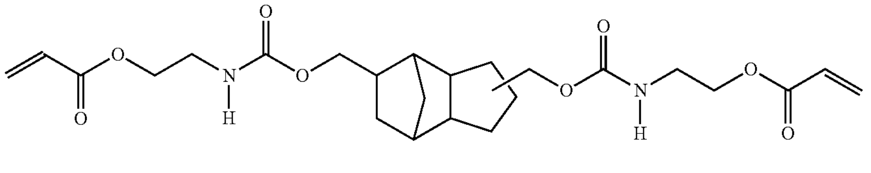

A di-functional urethane acrylate is preferably selected from di-functional urethane acrylates having a bivalent (ii) 10 to 30% by weight, such as up to 29.98% by weight, preferably 12 to 20% by weight of a mixture of at least two different urethane acrylates, in particular of a mixture of at least one di-functional urethane acrylate or di-functional urethane alkyl acrylate having a bivalent alicyclic group comprising a urethane of the idealised formula I and/or mixtures of the urethanes of formula I, as well as optionally mixture of isomers of the urethanes of formula I (see also formula Ia), in particular mixture of the 3,8-/3,9-/4,8-/3,10-/4,10-isomers and/or of the cis- and trans-isomers of the aforementioned compounds, with $R^1$ and $R^2$ each independently selected from H and alkyl with 1 to 8 C atoms, preferred is a mixture of at least three different urethane acrylates and/or urethane alkyl acrylates, in particular comprising di- to deca-functional urethane acrylates, (iii) 0.01 to 5% by weight of at least one di-, tri-, tetra- or multi-functional monomer not being a urethane acrylate or urethane (alkyl) acrylate, in particular not being a urethane (methyl) acrylate, (iv) 0.01 to 10% by weight of at least one initiator, of an initiator system, as well as optionally of at least one stabiliser, and optionally of at least one pigment, in particular the at least one pigment comprising fluorescence as well as colour pigment, the total composition of the composite material amounting to 100% by weight.

In an embodiment variant, it is preferred for the polymerisable composite material to be photochemically or photoinitiatedly polymerisable, respectively. Alternatively, it is preferred for the polymerisable composite material to be thermally polymerisable. A photochemically polymerisable composite is understood to mean a composite material polymerisable by means of a UV emission and/or by visible light (Vis emission), preferably a composite material polymerisable by means of a radiation source having emission maxima in the spectral region of 400 nm to 530 nm, preferably having a maximum or maxima in the spectral region of 440 to 500 nm. Particularly preferably, irradiation of the composite material is carried out for greater than or equal to 10 seconds, in particular per projection surface of the radiation source. Further preferred is an irradiation for greater than or equal to 15 seconds to 5 minutes, preferably for 10 to 30 seconds per projection surface of the radiation source. Suitable radiation sources generally include all usual radiation sources having an emission wave length, preferably emission maxima, in the spectral range of 440 to 480 nm and an intensity of greater than 500 $mW/cm^2$, in particular as used in dental field. A radiation source having an LED lamp is particularly preferred.

A thermally polymerisable composite material is presently understood to mean a composite material that may be polymerised at greater than or equal to 60 to 150° C., preferably at greater than or equal to 70 to 150° C., particularly preferably from 90 to 150° C. In this context, according to the invention it is further preferred for the volume shrinkage to be less than or equal to 1.5% (ISO 17304:2013).

Also a subject matter of the invention is a dental composite material obtainable by polymerisation i) using a UV/Vis radiation source, preferably using a Vis radiation source having emission maxima in the spectral region of 380 nm to 530 nm, preferably having at least one maximum or maxima in the spectral range of 400 to 500 nm, and optionally ii) at a pressure of 50 to 300 Mpa and/or elevated temperature, preferably at 90 to 150° C., or i) using a UV and/or Vis radiation source, preferably using a Vis radiation source having emission maxima in the spectral range of 380 to 530 nm, preferably having at least one maximum or maxima in the spectral range of 400 to 500 nm, and/or ii) at a pressure of 50 to 300 Mpa and/or elevated temperature, preferably at 90 to 150° C.

In one embodiment variant, it is particularly preferred for the inorganic filler component to consist of at least a dental glass or a mixture of dental glasses, in particular of an afore-mentioned average particle size and an amorphous metal oxide, in particular a non-agglomerated amorphous metal oxide, preferably a silanised amorphous metal oxide. The dental glass may preferably also be silanised. Preferably, silanization comprises acrylic functionalization.

The following dental glasses are preferably considered: aluminium silicate glasses or fluoroaluminium silicate glasses, fluoroaluminium silicate glasses having a boron content, barium aluminum silicate, strontium silicate, strontium borosilicate, lithium silicate and/or lithium aluminum silicate as well as mixtures of at least two of the aforementioned dental glasses. Amorphous spherical fillers based on oxide or mixed oxide, such as amorphous $SiO_2$, $ZrO_2$ or mixed oxides of $SiO_2$ and $ZrO_2$, may be used as metal oxide or as a mixture of amorphous metal oxides.

A subject matter of the invention is also a dental composite material comprising a) a dental glass of an average particle size $d_{50}$ of 1.8 μm with plus/minus 0.25 μm and preferably $d_{99}$ less than or equal to 20 μm, or b) a dental glass comprising a mixture of dental glasses of different fractions having average particle sizes with i) $d_{50}$ of 2 to 8 μm optionally with plus/minus 0.5 μm, in particular with 4 to 6 μm optionally with plus/minus 0.25 μm, ii) $d_{50}$ of 1.0 to 2.0 μm optionally with plus/minus 0.25 μm, in particular with 1.2 to 2.0 μm optionally with plus/minus 0.5 μm, preferably with 1.5 μm optionally with plus/minus 0.15 μm, and iii) $d_{50}$ of 0.5 μm to 1.2 μm optionally with plus/minus 0.15 μm, 0.7 to 0.9 μm optionally with plus/minus 0.5 μm, wherein the fractions of i) to ii) to iii) are present in the ratio of 1 to 4:1:4 to 8, in particular of 2 to 3:1:6 to 7. Particularly preferred is i) $d_{50}$ of 5 μm optionally with plus/minus 0.5 μm, ii) $d_{50}$ of 1.8 μm optionally with plus/minus 0.25 μm and iii) $d_{50}$ of 0.85 μm optionally with plus/minus 0.15 μm, wherein the fraction of i) to ii) to iii) are present in the ratio of 1 to 4:1:4 to 8, in particular of 2 to 3:1:6 to 7.

According to a preferred embodiment, the dental composite material comprises at least one dental glass, in particular a radiopaque dental glass, of an average particle size $d_{50}$ of 1.2 to 2.0 μm, preferably having an average particle size of 1.35 to 1.95 μm, in particular with $d_{50}$ of 1.8 μm optionally plus/minus 0.15 μm, and preferably with $d_{99}$ less than or equal to 10 μm. Particularly preferably, a dental glass is additionally present having an average particle size of $d_{50}$ of about 0.85 μm optionally plus/minus 0.1 μm, in particular plus/minus 0.05 μm, preferably plus/minus 0.03 μm, and preferably with $d_{99}$ less than or equal to 10 μm. A particularly preferred dental glass comprises barium aluminum borosilicate glass. Moreover, a barium aluminum silicate glass having a reflective index of n=1.52 to 1.55, preferably 1.53, is particularly preferred. A particularly preferred particle size distribution may be in the range of $d_{10}$ with greater than or equal to 0.2 μm to $d_{99}$ less than or equal to 20 μm, preferably less than or equal to 7.5 μm, preferably with $d_{10}$ greater than or equal to 0.4 μm to $d_{99}$ less than or equal to 7.5 μm and an average diameter $d_{50}$ of 0.7 to 7.5 μm.

According to a preferred embodiment, the dental composite material comprises (i) 70 to 85% by weight at least one inorganic filler component, at least one dental glass of an average particle size $d_{50}$ of 0.7 to 2.0 μm being present of greater than or equal to 50 to 80% by weight, based on the composite material having a total composition of 100% by weight, in particular of greater than or equal to 55 to 76% by weight, preferably greater than or equal to 60 to 75% by weight, particularly preferably greater than or equal to 60 to 71% by weight in the total composition of 100% by weight. Further preferably in combination with an amorphous silicon dioxide with 4 to 7.5% by weight in the total composition.

Furthermore, a subject matter of the invention is a dental composite material comprising (i) 70 to 85% by weight of at least one inorganic filler component comprising at least one dental glass comprising barium aluminum borosilicate glass, barium aluminum borofluor silicate glass, in particular silanised, preferably functionalised with methacryloxypropyl groups, as well as optionally at least one non-agglomerated amorphous metal oxide of a primary particle size of 2 to 150 nm, in particular of 2 to 100 nm, preferably of 2 to 45 nm, the amorphous metal oxide comprising silicon dioxide, precipitated silicon dioxide, pyrogenic silica, zirconium oxide, mixed oxides or mixtures thereof, in particular the metal oxides are silanised.

In order to achieve a high flexural strength, the dental composite material preferably comprises as inorganic filler component (i.1) 66 to 84% by weight of at least one dental glass, in particular from 68 to 78% by weight, alternatively from 75 to 78% by weight, and optionally (i.2) 2 to 10% by weight amorphous metal oxide, in particular from 3 to less than 10% by weight, preferably 4 to 8% by weight, in the total composition (ad 100% by weight). The ratio of dental glass to amorphous metal oxide preferably amounts to 20:1 to 7:1, preferably to 15:1 to 10:1.

composition of the composite material of 100% by weight. The particle size of the polymeric filler preferably is in the range of 10 to 200 micrometers, in particular of 30 to 90 micrometers, particularly preferably 20 to 50 micrometers. The polymeric particulate filler preferably is non spherical. Preferably, the polymeric particulate filler is present in the form of splintered polymer.

According to a particularly preferable embodiment variant, the dental composite material comprises (i) 70 to 85% by weight of at least one inorganic filler component comprising (i.1) 60 to 84% by weight, in particular from 66 to 78% by weight, preferably 66 to 70% by weight or 75 to 78% by weight of at least one dental glass of an average particle size $d_{50}$ of 0.7 to 7.5 μm, in particular of 1.8 μm optionally with an afore-mentioned standard deviation, as well as optionally (i.2) 2 to 34% by weight, in particular from 3 to 15% by weight, preferably 3 to 10% by weight, particularly preferably 4 to 10% by weight, further preferably 1 to 7.5% by weight, of at least one amorphous silanised metal oxide and/or pyrogenic silica of a primary particle size of 2 to 100 nm, preferably of 2 to 45 nm, based on the total composition, (ii) 10 to 30% by weight, in particular from 15 to 30% by weight, preferably 18 to 22% by weight, of a mixture of at least three different urethane acrylates and/or urethane alkyl acrylates, in particular of di- to deca-functional urethane acrylates and/or corresponding urethane alkyl acrylates, preferably from 15 to 19% by weight of at least one di-functional urethane acrylate and/or urethane alkyl acrylate comprising a urethane of the idealised formula I

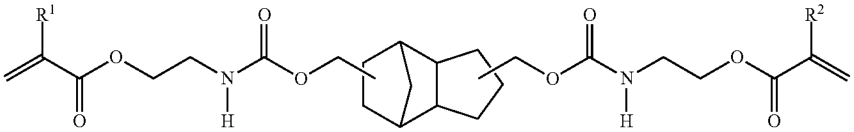
I

Preferably, from 85 to 99% by weight of at least one dental glass or a mixture of dental glasses, preferably from and/or mixture of said urethanes of formula I as well as of the isomers, in particular mixture

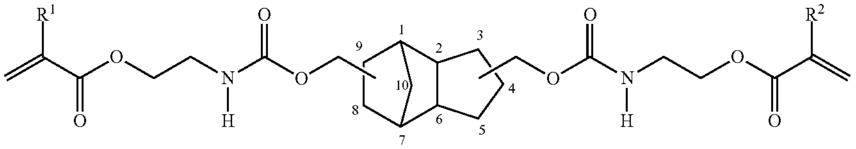
Ia 91 to 99% by weight, alternatively 92 to 99% by weight, and optionally greater than 1 to 13% by weight, in particular 8 to 15% by weight, alternatively 2 to 8% by weight amorphous metal oxide or a mixture of metal oxides, in particular pyrogenic silica and/or precipitated silicon dioxide, are present in the inorganic filler component.

In a preferred alternative, the composite material may comprise an amount of polymeric particulate fillers in addition to the inorganic filler component. The total amount of such polymeric particulate filler may amount to 0.01 to 15% by weight, preferably from 0.5 to 10% by weight, in the total of the 3,8-/3,9-/4,8-/3,10-/4,10-isomers of formula Ia and/or of the cis- and trans isomers of the afore-mentioned compounds, with $R^1$ and $R^2$ each independently selected from H and alkyl with 1 to 8 C atoms, and 5 to 6% by weight of a di-functional urethane acrylate having a bivalent alicyclic group with alkyl 1 to 10 C atoms and alkylene 3 to 20 C atoms, and optionally 0.1 to 2% by weight of at least one hexa-functional urethane acrylate and/or hexa-functional urethane methacrylate or dendritic urethane methacrylate, respectively, and (iii) 0.01 to 5% by weight, in particular 0.5 to 3% by weight, preferably 0.8 to 2.0% by weight, of at least one di-, tri-, tetra- or multi-functional monomer not being a urethane acrylate and not being a urethane alkyl acrylate, in particular at least one di-, tri-, tetra- or multi-functional methacrylic ester of polyethers, preferably dimethacrylate triethylene glycol, dimethacrylate tetraethylene glycol, and/or bis-(2'-oxa-3'-oxo-pentyl-4'-ene) tetrahydrodicyclopentadiene and isomers thereof, (iv) 0.01 to 10% by weight, in particular from 0.5 to 5% by weight, preferably 0.5 to 2% by weight, of at least one initiator or initiator system, preferably i) of at least one photoinitiator for the UV and/or Vis spectral region or a photoinitiator system for the UV and/or Vis spectral region, and optionally of at least one stabiliser, and/or ii) of at least one thermal initiator or of a thermal initiator system, as well as iii) optionally of at least one stabiliser, and iv) optionally of at least one pigment, in particular of a pigment mixture comprising a pigment selected from fluorescence and colour pigment, the total composition of the composite material amounting to 100% by weight.

The di- to deca-functional urethane acrylates or di- to deca-functional urethane alkyl acrylates are used as monomers and do not comprise peroxy groups.

According to a particularly preferred embodiment variant, the dental composite material comprises (ii) 10 to 30% by weight of a mixture of at least three different urethane acrylates and/or urethane alkyl acrylates, preferably of at least three different urethanes, the mixture comprising at least one di-functional urethane acrylate and/or urethane alkyl acrylate of the idealised formula I, see also formula Ia, decyl-9'-ene) tetrahydrodicyclopentadiene, bis-(2',7'-dioxa-3',8'-dioxo-4'-aza-9'-methyl-decyl-9'-ene) tetrahydrodicyclopentadiene, and optionally at least one di-functional urethane acrylate having a bivalent alicyclic group and/or urethane (meth)acrylate having a bivalent alicyclic group that is selected from bis-(4',7'-dioxa-3',8'-dioxo-2'-aza-decyl-9'-en) tetrahydrodicyclopentadiene, bis-(4',7'-dioxa-3',8'-dioxo-2'-aza-9'-methyl-decyl-9'-ene) tetrahydrodicyclopentadiene and/or mixtures thereof, as well as optionally of the 3,8-/3,9-/4,8-/3,10-/4,10-isomers and/or of the cis- and trans-isomers of the afore-mentioned compounds, and at least one further di-functional urethane (meth)acrylate, in particular at least one di-functional urethane acrylate having a bivalent alicyclic group and/or urethane methacrylate having a bivalent alicyclic group, as well as optionally at least one at least tetra-functional dendritic urethane acrylate and/or corresponding urethane methacrylate, preferably at least one hexa-functional dendritic urethane acrylate and/or urethane methacrylate. Particularly preferred are at least three different urethane (meth)acrylates selected from urethane acrylates and urethane methacrylates (based on the total composition of 100% by weigh).

According to a particularly preferred embodiment variant, the dental composite material comprises (ii) a mixture of at least two different urethane (meth)acrylates, preferably of three different urethane (meth)acrylates.

I

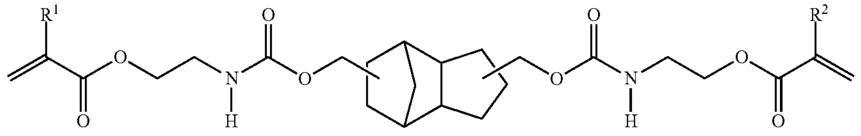

and/or mixture of said urethanes of formula I, as well as optionally mixtures of the 3,8-/3,9-/4,8-/3,10-/4,10-isomers and/or of the cis- and trans-isomers of the afore-mentioned compounds, with $R^1$ and $R^2$ each independently selected form H and alkyl with 1 to 8 C atoms, preferably H or methyl, and a di-functional urethane acrylate having a bivalent alkylene group and/or urethane alkyl acrylate having a bivalent alkylene group with alkyl from 1 to 10 C atoms, preferably with alkyl equal to methyl, and alkylene with 3 to 20 C atoms, preferably of three different urethane (alkyl) acrylates, as well as optionally at least one at least tetra-functional dendritic urethane (alkyl) acrylate, preferably at least one hexa-functional dendritic urethane (alkyl) acrylate, in particular urethane (meth)acrylate.

According to a particularly preferred embodiment variant, the dental composite material comprises (ii) 10 to 30% by weight of a mixture of at least two different urethanes selected from a mixture comprising at least one di-functional urethane acrylate and/or urethane alkyl acrylate comprising a urethane of the idealised formula I and/or mixtures of said urethanes of formula I, as well as optionally mixtures of the 3,8-/3,9-/4,8-/3,10-/4,10-isomers and/or of the cis- and trans-isomers of the afore-mentioned compounds, with $R^1$ and $R^2$ each independently selected from H and alkyl with 1 to 8 C atoms, such as bis-(2',7'-dioxa-3',8'-dioxo-4'-aza- The term (alkyl) acrylate or (meth)acrylate or urethane (alkyl) acrylate with (alkyl) in brackets or urethane (meth) acrylate with (meth) in brackets means that the term may comprise acrylates or urethane acrylates with or without alkyl groups or methyl groups. The alkyl groups preferably comprise 1 to 10 C atoms, preferably 1 to 2 C atoms in the said urethane alkyl acrylates. The alkyl groups preferably comprise 1 to 10 C atoms, preferably 1 to 2 C atoms in the said (alkyl) acrylates.

According to a particularly preferred embodiment variant, the dental composite material comprises ii) 10 to 30% by weight of a mixture of at least two different urethane (alkyl) acrylates, preferably of at least three different urethane (meth)acrylates, comprising at least a di-functional urethane (meth)acrylate of the general formula I and at least one di-functional urethane (meth)acrylate having a bivalent alkylene group, as well as optionally at least one at least tetra-functional dendritic urethane (meth)acrylate, preferably at least one hexa-functional dendritic urethane (meth) acrylate.

According to the invention, the urethane acrylate having a bivalent alicyclic group is selected from urethanes of the idealised formula I

I

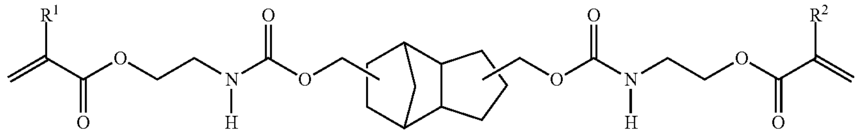

and/or mixtures of said urethanes of formular I, as well as optionally mixtures of the 3,8-/3,9-/4,8-/3,10-/4,10-isomers and/or of the cis- and trans-isomers of the afore-mentioned compounds, with $R^1$ and $R^2$ each independently selected from H and alkyl with 1 to 8 C atoms, such as preferably bis-(2',7'-dioxa-3',8'-dioxo-4'-aza-decyl-9'-ene) tetrahydrodicyclopentadiene, bis-(2',7'-dioxa-3',8'-dioxo-4'-aza-9'-methyl-decyl-9'-ene) tetrahydrodicyclopentadiene, particularly preferably bis-(2',7'-dioxa-3',8'-dioxo-4'-aza-decyl-9'-ene) tetrahydrodicyclopentadiene. The urethane of formula I is obtainable by a reaction of the corresponding tetrahydrodicyclopentadiene substituted twice with hydroxymethylene groups with the corresponding isocyanate of an acrylic derivative, such as 2-isocyanatoethyl methacrylate.

The di-functional urethane (alkyl) acrylate, urethane (alkyl) acrylate having a bivalent alkylene group or urethane (meth)acrylate having a bivalent alicyclic group is preferably selected from linear or branched urethane dimethacrylates being functionalised with a bivalent alkylene group, urethane dimethacrylate-functionalised polyethers having alkylene group(s), such as bis(methacryloxy-2-ethoxycarbonyl amino)alkylene, bis(methacryloxy-2-ethoxycarbonyl amino)-substituted polyalkylene ethers, preferably 1,6-bis (methacryloxy-2-ethoxycarbonyl amino)-2,4,4-trimethyl hexane, UDMA with the alternative name HEMA-TDMI. A bis(methacryloxy-2-ethoxycarbonyl amino)alkylene, wherein alkylene comprises linear or branched C3 to C20, preferably C3 to C6, is preferred, such as, particularly preferably, an alkylene substituted with methyl groups, such as HEMA-TMDI. The bivalent alkylene preferably comprises 2,2,4-trimethyl hexamethylene and/or 2,4,4-trimethyl hexamethylene.

The at least tetra-functional dendritic urethane methacrylate comprises tetra- to deca-functional dendritic urethane methacrylates.

It is also preferred for (ii) to comprise 10 to 30% by weight of a mixture of at least two different urethane (meth)acrylates, based on the total composition, preferably 15 to 20% by weight, such as at least one di-functional urethane of the general formula I and at least one hexa-functional dendritic urethane (meth)acrylate, optionally at least one di-functional urethane (meth)acrylate having a bivalent alkylene group.

Preferably, the composite material comprises 5 to 25% by weight, in particular from 15 to 19% by weight bis-(2',7'-dioxa-3',8'-dioxo-4'-aza-decyl-9'-ene) tetrahydrodicyclopentadiene, bis-(2',7'-dioxa-3',8'-dioxo-4'-aza-9'-methyl-decyl-9'-ene) tetrahydrodicyclopentadiene and/or mixtures thereof as well as optionally mixtures of the 3,8-/3,9-/4,8-/3,10-/4,10-isomers and/or of the cis- and trans-isomers of the afore-mentioned compounds, 1 to 15% by weight, in particular 5 to 6% by weight UDMA (1,6-bis(methacryloxy-2-ethoxycarbonyl amino)-2,4,4-trimethyl hexane), or HEMA-TMDI, respectively, and 0.1 to 5% by weight, preferably 0.2 to 2% by weight, particularly preferably 0.1 to 1% by weight of at least one tetra- to deca-functional dendritic urethane methacrylate, based on the total composition.

Preferably, the composite material comprises 10 to 20% by weight of a mixture of at least three different urethane (meth)acrylates, selected from 10 to 18% by weight comprising bis-(2',7'-dioxa-3',8'-dioxo-4'-aza-decyl-9'-ene) tetrahydrodicyclopentadiene, bis-(2',7'-dioxa-3',8'-dioxo-4'-aza-9'-methyl-decyl-9'-ene) tetrahydrodicyclopentadiene and/or mixtures thereof as well as optionally mixtures of the 3,8-/3,9-/4,8-/3,10-/4,10-isomers and/or of the cis- and trans-isomers of the afore-mentioned compounds, 3 to 8% by weight of a di-functional urethane (meth)acrylate having a bivalent alkylene group, in particular UDMA or HEMA-TMDI, respectively, and 0.1 to 2% by weight, preferably 0.2 to 2% by weight, particularly preferably 0.1 to 1% by weight of at least one tetra- to deca-functional dendritic urethane methacrylate, based on the total composition.

According to a further preferred embodiment, the dental composite material comprises as component (iii) 0.01 to 5% by weight of at least one di-, tri-, tetra- or multi-functional monomer not being a urethane (alkyl) acrylate and being selected from dimethacrylic esters of polyethers, bis-(2'-oxa-3'-oxo-pentyl-4'-ene) tetrahydrodicyclopentadiene or isomers thereof and tri-, tetra- or multi-functional methacrylic esters of polyethers.

Preferably, the content of components (iii) amounts to 0.15 to 15% by weight, in particular 0.15 to 5% by weight, particularly preferably 1.0 to 2% by weight, components (iii) being selected from dimethacrylic esters of a polyethers, such as preferably dimethacrylate polyethylene glycol, dimethacrylate polypropylene glycol. Dimethacrylate triethylene glycol (TEGDMA), diethylene glycol dimethacrylate (DEGMA) and dimethacrylate tetraethylene glycol (TEDMA) are particularly preferred Water as stabiliser may be added to the dental composite material to improve the consistency and the flow properties for the process-engineering processability. Stabilisers are preferably added to the composite material to prevent premature polymerisation and give the material a certain shelf life. The composite material comprises as preferred stabilisers in component (iv) at least one stabiliser selected from water, at least one benzophenone derivative, preferably alkoxy-substituted benzophenone and/or phenol derivative, such as 2-hydroxy-4-methoxybenzophenone, 2,6-bis(1,1-dimethyl)-4-methylphenol, or a mixture of the three stabilisers. The stabilisers are preferably present in 0.01 to 10% by weight in the total composition, particularly preferably from 0.7 to 10% by weight, in particular from 0.5 to 2% by weight. In addition, it is preferred for the composite material to contain 0.01 to 2% by weight water as stabiliser, preferably 0.1 to 1.0% by weight water.

At least one pigment comprising at least one fluorescence pigment and optionally at least one organic colour pigment and/or at least one inorganic colour pigment, in particular non-fluorescent colour pigments, are added to the composite material for optimal adjustment of the colour and natural aesthetic of the polymerised composite material. The at least one fluorescence pigment preferably is an organic fluorescence pigment, in particular a non-polymerisable organic fluorescence pigment, where appropriate comprising aryl carboxylic acid esters, aryl carboxylic acids, coumarin, rhodamine, naphthalene imide or a derivative of the respective substance. Inorganic fluorescence pigments may comprise $CaAl_4O_7:Mn^{2+}$, (Ba0.98Eu0.02) $MgAl_{10}O_{17}$, $BaMgF_4:Eu^{2+}$, Y(1.995)Ce(0.005)$SiO_5$.

The composite may comprise as pigments, in particular colour pigments, organic pigments as well as inorganic pigments, in particular comprising diethyl 2,5-dihydroxyterephthalate, N,N'-Bis(3,5-xylyl) perylene 3,4:9,10-bis(dicarbimide), copper phthalocyanine, titanate pigment, in particular chromium antimony titanate (rutile structure), spinel black, in particular pigments being based on iron oxide black ($Fe_3O_4$), wherein iron (Fe) is partially substituted by chromium and copper or nickel and chromium or manganese, zinc iron chromium spinel, brown spinel, ((Zn, Fe)(Fe, $Cr)_2O_4$), cobalt zinc aluminate blue spinel and/or titanium oxide. The pigments comprising fluorescence pigments and colour pigments preferably present in 0.01 to 10% by weight in the total composition, particularly preferably from 0.01 to 5% by weight, preferably from 0.01 to 1% by weight.

Selection of pigments has to be specifically adapted to the dental composite composition in order to achieve a homogeneous colour in both the polymerisable composite and the polymerised composite. Also the production of large blocks of material requires coordination with regard to the selection and to the concentration of the pigments in order to avoid undesirable discolourations due to the dimensioning of the polymerised blocks of material.

According to a further particularly preferred embodiment, the dental composite material comprises component (i) forming the filler component, wherein the filler component comprises (i.1) 85 to 95% by weight of at least one dental glass, in particular from 90 to 94.5% by weight, preferably from 92 to 94.5% by weight, and optionally (i.2) from 5 to 15% by weight amorphous metal oxide, in particular 5 to 10% by weight, preferably 5.5 to 8% by weight, in the filler component, wherein (i.1) and (i.2) amounts to 100% by weight of the filler component.

According to a further particularly preferred embodiment, the dental composite material comprises components (ii) and (iii) forming the monomer component, wherein the monomer component comprises (ii.1) 40 to 75% by weight of at least one urethane of formula I, in particular bis(2',7'-dioxa-3',8'-dioxo-4'-aza-decyl-9'-ene) tetrahydrodicyclopentadiene, bis(2',7'-dioxa-3',8'-dioxo-4'-aza-9'-methyl-decyl-9'-ene) tetrahydrodicyclopentadiene and/or mixtures thereof as well as optionally mixtures of the 3,8-/3,9-/4,8-/3,10-/4,10-isomers and/or of the cis isomers and trans isomers of the afore-mentioned compounds, and (ii.2) 21 to 38% by weight of at least one di-functional urethane (meth)acrylate having a bivalent alkylene group, as well as optionally (ii.3) 0.1 to 10% by weight, in particular 0.2 to 9% by weight of at least one tetra- to deca-functional dendritic urethane methacrylate, in particular a dendritic hexa-functional urethane methacrylate, and (iii) 1 to 14% by weight of at least one di-, tri-, tetra- or multi-functional monomer not being a urethane (alkyl) acrylate, wherein the monomers (ii.1), (ii.2), (ii.3) and (iii) amounts to 100% by weight in the monomer component.

According to a further preferred embodiment, the composite material may comprise:

(iv) 0.01 to 2% by weight photoinitiator for the UV and/or Vis spectral region or a photoinitiator system for the UV and/or Vis spectral region (visible light), and 0.01 to 2% by weight stabiliser.

Another subject matter of the invention is a polymerised dental composite material obtainable by polymerisation of the composite material according to the invention, in particular polymerisation by means of UV and/or Vis radiation, preferably by means of Vis radiation, particularly preferably by means of a radiation source that has emission maximal in the spectral range of 400 nm to 530 nm.

According to a particular preferred embodiment, a subject matter of the invention is a polymerised dental composite material comprising 70 to 85% by weight of at least one inorganic filler component comprising at least one dental glass of an average particle size $d_{50}$ in the range of 0.8 to 5.5 μm and preferably de less than or equal to 20 μm, preferably less than 7.5 μm, as well as optionally at least one amorphous silanised metal oxide, in particular precipitated silicon dioxide and/or pyrogenic silica of a primary particle size of 2 to 150 nm, preferably of 2 to 100 nm, particularly preferably of 2 to 45 nm, 10 to 30% by weight of at least one polymer, in particular co-polymer, being based on a polymerised mixture comprising at least one bis-urethane of formula I and at least one diurethane (meth)acrylate having a bivalent alkylene group, at least one tetra- to deca-functional dendritic urethane methacrylate, and at least one di-, tri-, tetra- or multi-functional methacrylic ester of polyethers, preferably dimethacrylate triethylene glycol, and 0.01 to 10% by weight of at least one pigment, in particular of at least one fluorescence pigment and of at least one organic colour pigment and/or of at least one inorganic colour pigment, the colour pigments preferably not doing fluoresce, the total composition of the composite material amounting to 100% by weight.

Furthermore, the polymerised composite material may be used for producing direct dental restorations, indirect dental restorations, dental prosthetic restorations comprising crowns, inlay, onlays, superstructures, artificial teeth, dental bridges, dental bars, spacers, abutments or veneers. The polymerised composite material may additionally be used as composite material for the production of direct adhesive dental restorations.

The following are also preferably considered to be urethane (meth)acrylates according to the invention: (ii) at least one urethane (meth)acrylate, in particular a urethane dimethacrylate, preferably a bis(methacryloxy-2-ethoxycabonyl amino)alkylene, diurethane acrylate oligomers, alkyl-functional urethane dimethacrylate oligomers, aromatic-functionalised urethane dimethacrylate oligomers, aliphatic unsaturated urethane acrylates, urethane bis(methacryloxy-2-ethoxycarbonyl amino)-substituted polyethers, aromatic diacrylate oligomers, aliphatic urethane diacrylate oligomers, aliphatic urethan diacrylates, hexa-functional aliphatic urethane resins, aliphatic urethane triacrylates, aliphatic urethane acrylate oligomers, unsaturated aliphatic urethane acrylates. Di-functional and multi-function urethane (meth) acrylates are preferred, such as, in particular, urethane di(meth)acrylate, the at least one (iii) urethane dimethacrylate is particularly preferably selected from linear or branched alkyl-functionalised urethane dimethacrylates, urethane dimethacrylate-functionalised polyethers, in particular bis(methacryloxy-2-ethoxycarbonyl amino)alkylene, bis(methacryloxy-2-ethoxycarbonyl amino)-substituted polyethers, preferably 1,6-bis(methacryloxy-2-ethoxycarbonyl amino)-2,4,4-trimethyl hexane. Suitable urethane (meth) acrylates are available under the following brand names: Ebecryl 230 (aliphatic urethane diacrylate), Actilane 9290, Craynor 9200 (diurethane acrylate oligomer), Ebecryl 210 (aromatic urethane diacrylate oligomers), Ebecryl 270 (aliphatic urethane diacrylate oligomers), Actilane 165, Actilane 250, Genomer 1122 (mono-functional urethane acrylate), Photomer 6210 (cas no. 52404-33-8, aliphatic urethane diacrylate), Photomer 6623 (hexa-functional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate). The urethane (meth)acrylates may preferably be selected from the afore-mentioned urethane (meth) acrylates or from a mixture of at least two different, preferably at least three different, afore-mentioned urethane (meth)acrylates.

The at least one di-, tri-, tetra- or multi-functional monomer not being a urethane (alkyl) acrylate, in particular not being a urethane (meth)acrylate, is preferably selected from at least one of the following monomers, in particular a mixture of monomers comprising bis-(2'-oxa-3'-oxo-pentyl-4'-ene) tetrahydrodicyclopentadiene (esters of Tricyclo [5.2.1.$^{02,6}$]decane dimethanol and two acrylates) and isomers thereof, 1,4-butandiol dimethacrylate (1,4-BDMA) or pentaerythritol tetraacrylate, bis-GMA monomer (bisphenol A glycidyl methacrylate), triethylene glycol dimethacrylate (TEGDMA) and diethylene glycol dimethacrylate (DEGMA), tetraethylene glycol di(meth)acrylate, decanediol di(meth)acrylate, dodecanediol di(meth)acrylate, hexyldecanediol di(meth)acrylate, trimethylol propane tri (meth) acrylate, pentaerythritol tetra(meth)acrylate as well as butanediol di(meth)acrylate, ethylene glycol di(meth)acrylate, polyethylene glycol di(meth)acrylate, ethoxylated/propoxylated bisphenol A di(meth)acrylate, a mixture comprising at least one of these (meth)acrylates and/or copolymers comprising one or at least two of the aforementioned monomers.

Typical di-functional monomers, also referred to as cross-linker and/or multi-crosslinker, include tri- or tetraethylene glycol di(meth)acrylate, BDMA, 1,4-butandiol dimethacrylate (1,4-BDMA), bis-GMA monomer (bisphenol A glycidyl methacrylate, an addition product of methacrylic acid and bisphenol A diglycidyl ether), diethylene glycol di(meth) acrylate, bisphenol A di(meth)acrylate, decanediol di(meth) acrylate, dodecanediol di(meth)acrylate, hexyldecanediol di(meth)acrylate as well as butanediol di(meth)acrylate, ethylene glycol di(meth)acrylate, polyethylene glycol di(meth)acrylate, ethoxylated/propoxylated bisphenol A di(meth)acrylates. The following di-functional monomers may also be added as diluting agents (low viscosity acrylates). Tri- and tetra-functional monomers and/or multi-crosslinkers comprise trimethylol propane tri (meth)acrylate, tris(2-hydroxyethyl) isocyanurate triacrylate, pentaerythritol tetraacrylate.

At least one of the following monomers may be present in the composite material in addition to the di-, tri- or multi-functional monomer or monomers, comprising at least one monomer, in particular a mixture of monomers of methyl methacrylate, ethyl methacrylate, propyl methacrylate, butyl methacrylate, n-hexyl methacrylate, 2-phenoxyethyl methacrylate, isobornyl methacrylate, isodecyl methacrylate, polypropylene glycol monomethacrylate, tetrahydrofuryl methacrylate, methyl acrylate, ethyl acrylate, propyl acrylate, butyl acrylate, n-hexyl acrylate, 2-phenoxyethyl acrylate, isobornyl acrylate, isodecyl acrylate, tetrahydrofuryl acrylate, hydroxyethyl acrylate, hydroxypropyl acrylate, hydroxyethyl methacrylate, hydroxypropyl methacrylate, benzyl-, furfuryl- or phenyl (meth)acrylate, a mixture containing at least one of these (meth)acrylates and/or copolymers comprising one or at least two of the aforementioned monomers.

Furthermore, a subject matter of the invention is a composite material comprising, preferably additionally, at least one or more substance(s) from the groups consisting of fillers, pigments, stabilisers, regulators, antimicrobial additives, UV-absorbing agents, thixotroping agents, catalysts and crosslinkers. Rather small amounts of said additives—as also of pigments, stabilisers and regulators—are used, e.g. a total of 0.01 to 3.0, in particular 0.01 to 1.0% by weight, based on the total composition of the composite material. Suitable stabilizers include e.g. hydroquinone monomethyl ether or 2,6-di-tert.-butyl 4-methyl phenol (BHT).

Preferably, the composite material comprises as component (iv) 0.01 to 10% by weight, in particular from 0.5 to 5% by weight, preferably 0.5 to 2% by weight, of at least one initiator or initiator system, preferably i) at least one photoinitiator for the UV and/or Vis spectral region or a photoinitiator system for the UV and/or Vis spectral region, and optionally at least one stabiliser, and optionally further usual additives, optionally pigment(s) or dye(s).

Particularly preferred photoinitiators comprise alpha-hydroxyphenyl ketone, benzildimethyl ketal or 2,4,6-trimethyl benzoyl diphenyl phosphine oxide, phenyl bis(2,4,6-trimethyl benzoyl) phosphine oxide, 2,4,6-trimethyl benzoyl phenyl phosphinic acid ethyl ester, and mixtures of at least two of the photoinitiators, bisacyl phosphine oxides (BAPO). Or also camphorquinone with amines selected from N,N-dimethyl p-toluidine, N-N-dihydroxyethyl p-toluidine and p-dimethyl aminobenzoic acid diethyl ester.

Typical stabilisers comprise 2,6-di-tert.-butyl 4-methyl phenol (BHT) or hydroquinone monomethyl ether (MEHQ), 2-hydroxy-4-methoxybenzophenone, HALS (Hindered Amine Light Stabilisers), benzotriazole ultraviolet absorbers (UVAs) and hydroxy phenyl triazines (HPT). Particularly suitable stabilisers are e.g. hydroquinone monomethyl ether or 2,6-di-tert.-butyl 4-methyl phenol (BHT).

Peroxides, hydroxyl peroxides, optionally azo compounds, or mixtures comprising them are suitable as initiators, in particular thermal initiators or initiator systems. Suitable thermal initiators may be used as radical initiators in the temperature range of 70 to 150° C., preferably of 90 to 150° C. Preferred thermal initiators comprise at least one initiator selected from: dilauroyl peroxide, di-tert.-butyl peroxide, tert.-butyl peroxy-2-ethyl hexanoate, dibenzoyl peroxide, dicumyl peroxide, dicumyl hydroperoxide, 2,2'-azobisisobutyronitrile, benzyl barbituric acid derivative, particularly preferably tert.-butyl peroxy-2-ethyl hexanoate, dibenzoyl peroxide, dicumyl peroxide, dicumyl hydroperoxide, azobisisobutyronitrile, benzyl barbituric acid derivative, such as phenyl benzyl barbituric acid, cyclohexyl benzyl barbituric acid.

The following initiators and/or initiator systems for auto- or cold-polymerisation comprise a) at least one initiator, in particular at least one peroxide and/or azo compound, in particular LPO: dilauroyl peroxide, BPO: dibenzoyl peroxide, t-BPEH: tert.-butyl peroxy-2-ethyl hexanoate, AIBN: 2,2'-azobis-(isobutyronitrile), DTBP: di-tert.-butyl peroxide, and, optionally, b) at least one activator, in particular at least one aromatic amine, such as N,N-dimethyl p-toluidine, N,N dihydroxyethyl p-toluidine and/or p-dimethyl aminobenzoic acid diethyl ester, or c) at least one initiator system selected from redox systems, in particular a combination selected from dibenzoyl peroxide, dilauroyl peroxide, and camphorquinone with amines selected from N,N dimethyl p-toluidine, N,N-dihydroxyethyl p-toluidine, and p-dimethyl aminobenzoic acid diethyl ester. The initiator may alternatively be a redox system comprising a peroxide, and a reduction agent selected from ascorbic acid, ascorbic acid derivative, barbituric acid or a barbituric acid derivative, sulfinic acid, sulfinic acid derivative, particularly preferred is a redox system comprising (i) barbituric acid or thiobarbituric acid or a barbituric acid derivative or thiobarbituric acid derivative, and (ii) at least one copper salt or copper complex, and (iii) at least one compound having an ionic halogen atom, particularly preferred is a redox system comprising 1-benzyl 5-phenyl barbituric acid, copper acetyl acetonate, and benzyl dibutyl ammonium chloride. Particularly preferably, the polymerisation in the two-component prosthetic base material is started by a barbituric acid derivative.

In general, initiators for the polymerisation reaction of cold- or auto-polymerising starting mixtures are considered to be those with which radical polymerisation reactions may be started. Preferred initiators are peroxides as well as azo compounds, such as, for example, the following: LPO: dilauroyl peroxide, BPO: dibenzoyl peroxide, t-BPEH: tert.-butyl peroxi-2-ethyl hexanoate, AIBN: 2,2'-azobis-(isobutyronitrile), DTBP: di-tert.-butyl peroxide.

In order to accelerate the initiation of radical polymerisation by peroxides, suitable activators, e.g. aromatic amines, may be added. Examples of suitable amines are N,N-dimethyl p-toluidine, N,N-dihydroxyethyl p-toluidine and p-dibenzyl aminobenzoic acid diethyl ester. In this context, the amines regularly function as co-initiators and are usually present in an amount of up to 0.5% by weight.

The following exemplary embodiments are intended to illustrate the invention without limiting the invention to these examples.

EXEMPLARY EMBODIMENT

Testing method for determining the fracture toughness according to ISO-13586:2000 Test specimens (CT specimens) according to ASTM E 1820-13 and ISO 13586:2000, with alternatives ratios for W/B 2≤W/B≤4.

The fracture toughness of the composition to be measured is determined on test specimens (CT specimens) having the following dimensions W (according to ASTM 1820-13) and w (according to ISO 13586)=10 mm, B (according to ASTM 1820-13) und h (according to ISO 13586:2000)=5 mm, using the ratio or the proportions of the dimensions of the test specimens according to the specifications of ASTM E 1820-13 and ISO 13586.

At first, test specimens (cuboids) having a thickness of 5 mm and a base area/deck area of 12.0×12.5 mm are produced. Light curing or photo-polymerisation, respectively, was carried out by means of irradiation with blue light, wherein a total of five spots (projection surfaces) were irradiated for 20 seconds respectively (Translux 2 Wave, KULZER GmbH).

A notch (approx. 0.55 W) centrally and perpendicularly aligned to a longitudinal edge is made using a 1 mm rotating cutting tool. Holes perpendicularly made in the base/deck area are drilled to receive pins my means of a cutting tool having a diameter of 2 mm that are arranged at the same position as provided for the specimens of (ASTM 1820-13 and ISO 13583:2000).

A cut is made in the top of the centrally located notch by means of a razor blade to create a crack having a diameter of less than ≤8 μm. The length of the crack ($a_i$) is measured by means of an optical microscope before the measurement is carried out. The changing crack length $a_i$ is measured under the impact of defined mechanical forces.

FIG. 1*a*: Cross section of the test specimen, FIG. 1*b*: Top view onto the test specimen. With legend of refence numerals and labellings and description of the measurement setup.

LEGEND w=distance between the center point of the two holes and the opposite test specimen edge;

B=width of the entire test specimen; $l_1$=length; $l_2$=distance between the center point of the two holes being symmetrically arranged to the crack plane +/−0, 005w; B=thickness R=radius; a=crack length; P=force $$B=1.25w+/-0.01w; l_1=1.2w+/-0.01w, l_2=0.55w+/-0.0005w, R=0.125w+/-0.005w, 0.4w<h<0.6w; 0.45w\leq a\leq 0.55w$$

The pins and holes are intended to have a smooth surface and a loose fit to avoid friction.

$$K_{Ic}=[P/h\cdot W^{0.5}]f(a_i/W)$$

$$f(a_i/W)=\frac{\left\{\left(2+\frac{a_i}{W}\right)\left[0.886+4.64\left(\frac{a_i}{W}\right)-13.32\left(\frac{a_i}{W}\right)^2+14.72\left(\frac{a_i}{W}\right)^3-5.6\left(\frac{a_i}{W}\right)^4\right]\right\}}{\left(1-\frac{a_i}{W}\right)^{3/2}}$$

Thereafter, the test specimens are fixed in a universal testing machine (Zwick/Roell) using metallic pins that are guided through the holes. Subsequently, a defined tensile force (P) is applied via the pins the to the test specimen until break at a speed of 1 mm/min. The tensile force (P), the thickness (B) and the width (W) as well as the crack length $a_i$, the fracture toughness $K_{Ic}$ are calculated according to the following formula.

TABLE 1a

Compositions according to the invention Examples 1 to 2

| | | Example 1 | | Example 2 | |
|---|---|---|---|---|---|
| dental glass | average diameter $d_{50}$ = 1.8 μm or 1.5 μm $d_{99}$ < 20 μm | 1.8 μm | | 1.5 μm | |
| | | wt.-% | g | wt.-% | g |
| dental glass | barium aluminum borofluor silicate glass (silanised) | 75-78 | 75-78 | 66-70 | 66-70 |
| metal oxide | amorphous $SiO_2$ | 4.5-5 | 4.5-5 | 5-6 | 5-6 |
| urethane (meth)-acrylate | bis-(2',7'-dioxa-3',8'-dioxo-4'-aza-decyl-9'-ene) tetrahydro-dicyclopentadiene | 11-13 | 11-13 | 14-15 | 14-15 |
| | urethane methacrylate dendrimer, hexa-functional | 0.5-0.7 | 0.5-0.7 | 0.6-0.8 | 0.6-0.8 |
| | 7,7,9-trimethyl 4,13-dioxo-3,14-dioxa-5,12-diaza-hexadecane 1,16-diyl bismethacrylate | 4-5 | 4-5 | 5-5.5 | 5-5.5 |
| di- to multi-functional monomers | dimethacrylate triethylene glycol | 1.0-1.1 | 1.0-1.1 | 1.2-1.3 | 1.2-1.3 |

TABLE 1a-continued

| Compositions according to the invention Examples 1 to 2 | | Example 1 | | Example 2 | |
|---|---|---|---|---|---|
| initiator system | camphorquinone | 0.02 | 0.02 | 0.02 | 0.02 |
| | N,N-dimethyl 4-aminobenzoic acid ester, such as 2-n-butoxaethyl ester | 0.07 | 0.07 | 0.08 | 0.08 |
| stabiliser | 6-bis(1,1-dimethyl-ethyl) 4-methyl phenol | 0.04 | 0.04 | 0.04 | 0.04 |
| pigments | | 0.1-0.6 | 0.1-0.6 | 0.1-0.6 | 0.1-0.6 |

TABLE 1b

| Compositions according to the invention Examples 3 to 5 | | Example 3 | | Example 4 | | Example 5 | |
|---|---|---|---|---|---|---|---|
| dental glass | average diameter $d_{50}$ | 0.85 µm | | 0.85 µm | | 0.85 µm | |
| | | wt.-% | g | wt.-% | g | wt.-% | g |
| dental glass | barium aluminium borofluor silicate glass (silanised) | 74.00% | 74 | 75.60% | 75.6 | 72.36% | 72.36 |
| metal oxide | amorphous $SiO_2$ | 5.00% | 5 | 4.70% | 4.7 | 5.32% | 5.32 |
| urethane (meth)-acrylate | bis-(2',7'-dioxa-3',8'-dioxo-4'-aza-decyl-9'-ene) tetrahydro-dicyclopentadiene | 12.80% | 12.8 | 12.28% | 12.28 | 14.00% | 14 |
| | urethane methacrylate oligomer hexa-functional | 0.65% | 0.65 | 0.58% | 0.58 | 0.67% | 0.67 |
| | 7,7,9-trimethyl 4,13-dioxo-3,14-dioxa-5,12-diaza-hexadecane 1,16-diyl bismethacrylate | 4.50% | 4.5 | 4.55% | 4.55 | 5.19% | 5.19 |
| di- to multi-functional monomers | 1,2-bis(2-(methacryl-oyloxy)ethoxy)ethane | 0.85% | 0.85 | 0.87% | 0.87 | 1.00% | 1 |
| initiator system | tert.-butyl peroxy-2-ethyl hexanoate | 0.50% | 0.5 | 0.41% | 0.41 | 0.40% | 0.4 |
| stabiliser | 2-hydroxy-4-methoxy-benzophenone | 0.30% | 0.3 | 0.25% | 0.25 | 0.28% | 0.28 |
| | water | 0.70% | 0.7 | 0.66% | 0.66 | 0.64% | 0.64 |
| pigments | organic/inorganic pigments (e.g. $TiO_2$) | 0.70% | 0.7 | 0.1% | 0.1 | 0.14% | 0.14 |

TABLE 1c

| Compositions according to the invention Examples 6 to 8 | | Example 6 | | Example 7 | | Example 8 |
|---|---|---|---|---|---|---|
| dental glass | average diameter $d_{50}$ and $d_{99}$ <20 µm | 0.85 µm | | 0.85 µm | | 2.0 µm |
| | | wt.-% | g | wt.-% | g | wt.-% |
| dental glass | barium aluminium borofluor silicate glass (silanised) | 75-78 | 75-78 | 66-70 | 66-70 | |
| feldspar | | | | | | 66-70 |
| metal oxide | amorphous $SiO_2$ | 4.5-5 | 4.5-5 | 5-6 | 5-6 | 5-6 |
| urethane (meth)-acrylate | bis-(2',7'-dioxa-3',8'-dioxo-4'-aza-decyl-9'-ene) tetrahydro-dicyclopentadiene | 11-13 | 11-13 | 14-15 | 14-15 | 14-15 |

TABLE 1c-continued

| Compositions according to the invention Examples 6 to 8 | | | | | | |
|---|---|---|---|---|---|---|
| | | Example 6 | | Example 7 | | Example 8 |
| | urethane methacrylate dendrimer, hexa-functional | 0.5-0.7 | 0.5-0.7 | 0.6-0.8 | 0.6-0.8 | 0.6-0.8 |
| | 7,7,9-trimethyl 4,13-dioxo-3,14-dioxa-5,12-diaza-hexadecane 1,16-diyl bismethacrylate | 4-5 | 4-5 | 5-5.5 | 5-5.5 | 5-5.6 |
| di- to multi-functional monomers | 1,2-Bis(2-(methacryl-oyloxy)ethoxy)ethane (TEGDMA) | 1.0-1.1 | 1.0-1.1 | 1.2-1.3 | 1.2-1.3 | 1.2-1.4 |
| initiator system | tert.-butyl peroxy-2-ethyl hexanoate | | | | | 0.37 |
| | camphorquinone | 0.2 | 0.2 | 0.2 | 0.2 | |
| | N,N-dimethyl 4-aminobenzoic acid ester, such as 2-n-butoxaethyl ester | 0.07 | 0.07 | 0.08 | 0.08 | |
| stabiliser | 2-hydroxy-4-methoxy-benzophenone | 0.04 | 0.04 | 0.04 | 0.04 | 0.04 |
| | water | | | | | 0.6 |
| pigments | e.g. $TiO_2$ | 0.1-0.6 | 0.1-0.6 | 0.1-0.6 | 0.1-0.6 | 0.1-0.6 |

TABLE 1d

| Compositions according to the invention Examples 9 and 10 | | | | | |
|---|---|---|---|---|---|
| | | Example 9 | | Example 10 | |
| dental glass | average diameter $d_{50}$ 0.85 μm and $d_{99}$ < 20 μm | 0.85 μm | | 0.85 μm | |
| | | wt.-% | g | wt.-% | g |
| dental glass | barium aluminium borofluor silicate glass (silanised) | 40 | 40 | 79 | 79 |
| metal oxide | amorphous $SiO_2$ | 5 | 5 | 5 | 5 |
| urethane (meth-) acrylate | bis-(2',7'-dioxa-3',8'-dioxo-4'-aza-decyl-9'-ene) tetrahydrodicyclopentadiene | 46.80 | 46.80 | 7.8 | 7.8 |
| | urethane methacrylate dendrimer, hexa-functional | 0.65 | 0.65 | 0.65 | 0.65 |
| | 7,7,9-trimethyl 4,13-dioxo-3,14-dioxa-5,12-diaza-hexadecane 1,16-diyl bismethacrylate | 4.5 | 4.5 | 4.5 | 4.5 |
| di- to multi-functional monomers | 1,2-bis(2-(methacryloyloxy) ethoxy) ethane (TEGDMA) | 0.85 | 0.85 | 0.85 | 0.85 |
| initiator system | tert.-butyl peroxy-2-ethyl hexanoate | 0.5 | 0.5 | 0.5 | 0.5 |
| | camphorquinone | 0.2 | 0.2 | 0.2 | 0.2 |
| | N,N-dimethyl-4-aminobenzoic acid ester, such as 2-n-butoxaethyl ester | 0.16 | 0.16 | 0.16 | 0.16 |
| stabiliser | 2-hydroxy-4-methoxy-benzophenone | 0.30 | 0.30 | 0.30 | 0.30 |
| | water | 0.50 | 0.50 | 0.50 | 0.50 |
| pigments | e.g. $TiO_2$ | 0.7 | 0.7 | 0.7 | 0.7 |

TABLE 2

| Comparative examples (VG) 1 to 2 | | | | | |
|---|---|---|---|---|---|
| | | VG 1 | | VG 2 | |
| dental glass | average diameter $d_{50}$ = 1.8 μm and $d_{99}$ < 20 μm | 1.8 μm | | 1.8 μm | |
| | | wt.-% | g | wt.-% | g |
| dental glass | barium aluminium borofluor silicate glass (silanised) | 75-78 | 75-78 | 66-70 | 66-70 |
| metal oxide | amorphous $SiO_2$ $d_{50}$ = 20 nm | 4.5-5 | 4.5-5 | 5-6 | 5-6 |

TABLE 2-continued

| Comparative examples (VG) 1 to 2 | | | | | |
|---|---|---|---|---|---|
| | | VG 1 | | VG 2 | |
| | urethanr methacrylate dendrimer, hexa-functional | 0.5-0.7 | 0.5-0.7 | 0.6-0.8 | 0.6-0.8 |
| | 7,7,9-trimethyl 4,13-dioxo-3,14-dioxa-5,12-diaza-hexadecane 1,16-diyl bismethacrylate | 4-5 | 4-5 | 5-5.5 | 5-5.5 |
| di- to multi-functional monomers | dimethacrylate triethylene glycol | 1.0-1.1 | 1.0-1.1 | 1.2-1.3 | 1.2-1.3 |
| | bs-(2'-oxa-3'-oxo-pentyl-4'-ene) tetrahydrodicyclopentadiene | 11-13 | 11-13 | 14-15 | 14-15 |
| initiator system | camphorquinone | 0.02 | 0.02 | 0.02 | 0.02 |
| | N, N-dimethyl 4-aminobenzoic acid ester, such as 2-n-butoxaethyl ester | 0.07 | 0.07 | 0.08 | 0.08 |
| stabiliser | 2,6-bis(1,1-dimethyl ethyl) 4-methyl phenol | 0.04 | 0.04 | 0.04 | 0.04 |
| pigments | | 0.1-0.6 | 0.1-0.6 | | |

TABLE 3

| Comparative example (VG) 3 as VG3a to d in variation within the indicated ranges | | | |
|---|---|---|---|
| | | VG 3 | |
| dental glass | average diameter $d_{50}$ = 0.85 μm, $d_{99}$ = < 5 μm | 0.85 μm | |
| | | wt.-% | g |
| dental glass | barium aluminium borofluor silicate glass (silanised) | 62-80 | 62-80 |
| metal oxide | amorphous $SiO_2$, $d_{50}$ = 5-10 nm | 6.2-8.1 | 6.2-8.1 |
| | bis-GMA | 11.8-16.2 | 11.8-16.2 |
| | dimethacrylate triethylene glycol | 5.4-7.4 | 5.4-7.4 |
| | camphorquinone | 0.03 | 0.03 |
| di- to multi-functional monomers | N,N-dimethyl 4-aminobenzoic acid ester, such as 2-n-butoxaethyl ester | 0.04 | 0.04 |
| stabiliser | 2,6-bis(1,1-dimethyl ethyl) 4-methyl phenol | 0.03-0.12 | 0.03-0.12 |
| pigments | | 0.1-0.2 | 0.1-0.2 |

Irradiation method of the surface of the test specimens with blue light (emission maximum approx. 440 to 460 nm) with 5 projection surfaces on the surface of the test specimen with respectively 1×20 seconds of the samples in Table 4. Thermal curing for further polymerisation indicated in Table 4 was carried out for approx. 3 h at 95° C.

TABLE 4

| Results of the fracture toughness measurement | | | | |
|---|---|---|---|---|
| | Irradiation method | | Irradiation method subsequent thermal curing 3 h at 95° C. | |
| Composition* | $K_{IC}$ [MPa√m] | Stdev | $K_{IC}$ [MPa√m] | Stdev |
| VG3a | 0.7 | 0.2 | | |
| VG3b | 0.8 | 0.2 | | |
| VG3c | | | 1.0 | 0.2 |
| VG3d | | | 0.9 | 0.2 |
| Example 2 | 2.0 | 0.1 | | |
| Example 2 | | | 1.9 | 0.2 |
| Example 1 | 2.0 | 0.3 | | |
| Example 1 | | | 2.3 | 0.3 |
| Example 4 | | | 1.7 | 0.2 |
| VG 1 | 1.4 | 0.2 | | |
| VG 2 | 1.3 | 0.3 | | |

*Different polymerisation conditions of VG3a to VG3d, Example 4 with UV/Vis 1 × 60 seconds irradiated and subsequently thermally polymerised for approx. 3 h 95° C.

The results of the fracture toughness measurement on the test specimens only radiation polymerised of the comparative examples with bis-GMA as a component in the polymer matrix show quite low values for the fracture toughness (VG3a, VG3b) which can no longer be significantly improved even in combination of a preceding irradiation with subsequent thermal curing for 3 hours at 98° C. (VG3c, VG3d).

Even the examples with a TCD ester as component of the polymer matrix in examples VG1 and VG2 already show improved values compared to the matrix based on bis-GMA. Significantly better values of 1.9 and 2.3 MPa·$m^{1/2}$ for the fracture toughness are obtained with the composite materials according to the invention based on bis-(2',7'-dioxa-3',8'-dioxo-4'-aza-decyl-9'-ene) tetrahydrodicyclopentadiene as well as its isomers in the polymer matrix.

The invention claimed is:

1. Polymerisable dental composite material, comprising:

(i) an inorganic filler component comprising:

(i.1) 70 to 84% by weight of at least one dental glass, wherein a) the dental glass has an average particle size $d_{50}$ of 1.8 μm, or b) the dental glass comprises a mixture of dental glasses having an average particle size, with i) $d_{50}$ of 2 to 8 μm, ii) $d_{50}$ of 1.0 to 2.0 μm, and iii) $d_{50}$ of 0.5 μm to 2 μm, the fractions of i) to ii) to iii) being present in a ratio of 1 to 4:1:4 to 8, and (i.2) 2 to 10% by weight amorphous metal oxide, (ii) a mixture of at least three different urethane acrylates, the mixture comprising 10 to 18% by weight of at least one urethane acrylate having a bivalent alicyclic group of the idealised formula I

I

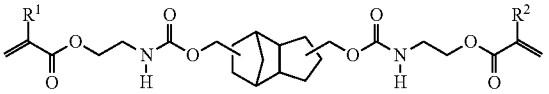

and/or mixtures of said urethanes of formula I, as well as optionally mixtures of the isomers of the aforementioned compounds with $R^1$ and $R^2$ each independently selected from H and alkyl having 1 to 8 C-atoms, and 3 to 8% by weight of at least one further di-functional urethane acrylate and/or urethane (alkyl) acrylate having a bivalent alkylene group and not satisfying formula I, and 0.2 to 2% by weight of at least one at least tetra-functional dendritic urethane methacrylate comprising tetra- to deca-functional dendritic urethane methacrylates, (iii) 0.01 to 2% by weight of at least one substance selected from the group consisting of di-methacrylic esters of polyethers, tri-, tetra- or multi-functional methacrylic esters of polyethers and bis-(2'-oxa-3'-oxo-pentyl-4'-ene) tetrahydrodicyclopentadiene and isomers thereof, (iv) 0.01 to 10% by weight of at least one initiator, of an initiator system, as well as optionally of at least one stabiliser, and optionally of at least one pigment, wherein each % by weight is based on a total weight of the composite material, the total weight of the composite material amounting to 100% by weight.

2. Dental composite material according to claim 1, wherein the at least one dental glass has an average particle size $d_{50}$ of 0.5 to 10 μm.

3. Dental composite material according to claim 1, wherein the amorphous metal oxide comprises at least one non-agglomerated amorphous metal oxide having a primary particle size of 2 to 150 nm, and the amorphous metal oxide optionally comprising precipitated silicon oxide, pyrogenic silica, zirconium oxide or mixed oxides.

4. Dental composite material according to claim 1, wherein the at least one stabiliser comprises water, at least one benzophenone derivative and/or at least one phenol derivative.

5. Dental composite material according to claim 1, wherein it further comprises (v) 0.01 to 15% by weight of a polymeric particulate filler, the total composition of the composite material amounting to 100% by weight.

6. Polymerised dental composite material obtainable by polymerising the composite material according to claim 1, i) using a UV- and/or VIS-radiation source having emission maxima in the spectral range of 400 nm to 530 nm, and/or ii) at a pressure of 50 to 300 MPa and/or iii) at an elevated temperature of 90 to 150° C.

7. Polymerised dental composite material according to claim 6, comprising:

(ii) at least one polymer based on the mixture, wherein the mixture comprises:

3 to 8% by weight of the at least one further di-urethane acrylate having a bivalent alkylene group and not satisfying formula I, and (iv) 0.01 to 10% by weight of the at least one pigment, and of at least one organic dying pigment and/or at least one inorganic dying pigment, wherein each % by weight is based on a total weight of the composite material, the total composition weight of the composite material amounting to 100% by weight.

8. Polymerised dental composite material according to claim 6, wherein the polymerised dental composite material is present in the form of a block of material, wherein the block of material is present as three-dimensional geometric form body.

* * * * *